United States Patent
Cho et al.

(10) Patent No.: US 6,849,652 B1
(45) Date of Patent: Feb. 1, 2005

(54) 1,2,4-TRIAZOLE DERIVATIVE, METHOD FOR PREPARING THE SAME, AND PHARMACEUTICAL COMPOSITION CONTAINING THE SAME

(75) Inventors: Il Hwan Cho, Seoul (KR); Dong Hyun Ko, Gwacheon (KR); Myeong Yun Chae, Seongnam (KR); Taerho Kim, Seongnam (KR); Kyoung Rae Kang, Seoul (KR); Jong Hoon Kim, Anyang (KR); Sung Hak Jung, Seoul (KR); Sang Wook Park, Suwon (KR); Hyung Ok Chun, Gunpo (KR); Hyung Chul Ryu, Yongin (KR); Ji Young Noh, Busan (KR); Hyun Jung Park, Jeonrabuk-do (KR); Jie Eun Park, Wonju (KR); Young Mee Chung, Suwon (KR)

(73) Assignee: CJ Corp. (KR)

(*) Notice: Subject to any disclaimer, the term of this patent is extended or adjusted under 35 U.S.C. 154(b) by 0 days.

(21) Appl. No.: 10/631,594

(22) Filed: Jul. 31, 2003

(30) Foreign Application Priority Data

Nov. 21, 2002 (KR) .................... 10-2002-0072688

(51) Int. Cl.[7] .................. A61K 31/4196; C07D 249/08; A61P 29/00
(52) U.S. Cl. .................... 514/383; 548/269.4
(58) Field of Search .................. 548/269.4; 514/383

(56) References Cited

U.S. PATENT DOCUMENTS

| | | | | |
|---|---|---|---|---|
| 5,444,148 A | * | 8/1995 | Alewelt et al. | 528/196 |
| 5,466,823 A | | 11/1995 | Talley et al. | 548/377.1 |
| 5,633,272 A | | 5/1997 | Talley et al. | 514/378 |

FOREIGN PATENT DOCUMENTS

| EP | 1099695 A1 | * | 11/1999 |
|---|---|---|---|
| WO | 95/00501 | | 1/1995 |

OTHER PUBLICATIONS

News and Views; "Towards a better aspirin"; Author: John Vane; Nature, vol. 367; Jan. 20, 1994; pp. 215–216.
Meeting Report; "COX–1 and COX–2: Toward the Development of More Selective NSAIDs"; Authors: Bruno Battistini, Regina Botting and Y.S. Bakhle; DN & P 7 (8); Oct. 1994; pp. 501–512.
Chapter 19; "Selective Cycloozygenase Inhibitors"; Authors: David B. Reitz and Karen Seibert; Annual Reports in Medicinal Chemistry–30; Academic Press, Inc.; 1995; pp. 179–188.

Pergamon; "Synthesis and Biological Evaluation of 2,3–Diarylthiophenes as Selective COX–2 and COX–1 Inhibitors"; Authors: Yves Leblanc, Jacques Yves Gauthier, Diane Ethier, Jocelyne Guay, Joseph Mancini, Denis Riendeau, Philip Tagari, Philip Vichers, Elizabeth Wong and Petpiboon Prasit; Bioorganic & Medicinal Chemistry Letters, vol. 5, No. 18; Elsevier Science Ltd.; 1995; pp. 2123–2128.

"Synthesis and Biological Evaluation of the 1, 5–Diarylpyrazole Class of Cycloozygenase–2 Inhibitors: Identification of 4–[5–(4–Methylphenyl)–3–(trifluoromethyl)–1 H–pyrazol–1–yl]benzenesulfonamide(SC–58635, Celecoxib)"; Authors: Thomas D. Penning, et al.; Journal of Medicinal Chemistry vol. 14, No. 9; American Chemical Society; 1997; pp. 1347–1365.

"Current Perspective Recent advances in the management of colorectal cancer"; Authors: E. Van Cutsem, M. Dicato, J. Wils; European Journal of Cancer 37; Elsevier Science Ltd.; 2001; pp. 2302–2309.

Monthly Focus; Central & Peripheral Nervous Systems; "Anti–inflammatory drugs: a hope for Alzheimer's disease?"; Authors: Michael Hull, Klaus Lieb & Bernd L. Fiebich; Asley Publications Ltd.; 2000; pp. 671–683.

* cited by examiner

Primary Examiner—Rita Desai
Assistant Examiner—Robert Shiao
(74) Attorney, Agent, or Firm—Cantor Colburn LLP

(57) ABSTRACT

A 1,2,4-triazole derivative of formula 1 or a non-toxic salt thereof, a preparation method thereof, and a pharmaceutical composition containing the derivative or the salt as an active ingredient are provided:

Formula 1

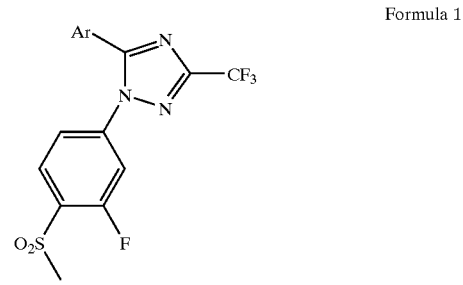

wherein, Ar represents naphthyl; 3,4-methylenedioxyphenyl: phenyl; or phenyl substituted with the group selected from $C_1$–$C_6$ alkyl, $C_1$–$C_6$ alkoxy, or halogen.

4 Claims, No Drawings

1,2,4-TRIAZOLE DERIVATIVE, METHOD FOR PREPARING THE SAME, AND PHARMACEUTICAL COMPOSITION CONTAINING THE SAME

BACKGROUND OF THE INVENTION

This U.S. non-provisional application claims priority under 35 U.S.C. §119 to Korean Patent Application No. 2002-72688, filed on Nov. 21, 2002, in the Korean Intellectual Property Office, the contents of which are incorporated herein by reference in its entirety.

1. Field of the Invention

The present invention relates to a 1,2,4-triazole derivative or a non-toxic salt thereof, a method for preparing the same, and a pharmaceutical composition containing the same as an active ingredient.

2. Description of the Related Art

Most nonsteroidal antiinflammatory agents are responsible for blocking enzyme, cyclooxygenase (COX) or prostaglandin G/H synthase, to reduce inflammation, pain, or fever. In addition, they inhibit uterus contraction caused by hormones and also inhibit growth of several cancers. Cyclooxygenase-1 (COX-1) was first discovered in bovine. The COX-1 is constitutively expressed in a variety of cell types. Unlike the COX-1, cyclooxygenase-2 (COX-2) is a recently discovered isoform of cyclooxygenase that can be easily induced by mitogen, endotoxin, hormone, growth factor, or cytokine.

Prostaglandin is a potent mediator for various pathological and physiological processes. The COX-1 plays important physiological roles such as in the release of endogenous prostaglandin, the maintenance of the shape and the function of stomach, and the blood circulation in the kidney. On the other hand, the COX-2 is induced by an inflammatory factor, hormone, a growth factor, or cytokine. Therefore, the COX-2 is involved in pathological processes of prostaglandin, unlike the constitutive COX-1. In this regard, selective inhibitors of the COX-2 produce fewer and less side effects in terms of action mechanism in comparison with conventional nonsteroidal antiinflammatory agents. In addition, they reduce inflammation, pain, and fever and inhibit uterus contraction caused by hormones and growth of several cancers. In particular, they are effective in decreasing side effects such as stomach toxicity and kidney toxicity. Still furthermore, they inhibit the synthesis of contractile prostanoid, thereby leading to suppression of the contraction of smooth muscles. Therefore, they help in preventing premature birth, menstrual irregularity, asthma, and eosinophilic disease.

Recently, it was reported that nonsteroidal antiinflammatory agents are effective in treating large intestine cancer [European Journal of Cancer, Vol 37, p2302, 2001], prostate cancer [Urology, Vol 58, p127, 2001], and dementia [Exp. Opin. Invest. Drugs, Vol 9, p671, 2000].

In addition, it is anticipated that selective inhibitors of the COX-2 would be effective in treating osteoporosis and glaucoma. Utility of selective inhibitors of the COX-2 is well described in publications [John is Vane, "Towards a Better Aspirin" in Nature, Vol. 367, pp215–216, 1994; Bruno Battistini, Regina Botting and Y. S. Bakhle, "COX-1 and COX-2: Toward the Development of More Selective NSAIDs" in Drug News and Perspectives, Vol. 7, pp501–512, 1994; David B. Reitz and Karen Seibert, "Selective Cyclooxygenase Inhibitors" in Annual Reports in Medicinal Chemistry, James A. Bristol, Editor, Vol. 30, pp179–188, 1995].

Various selective COX-2 inhibitors having different structures are known. Among them, a selective COX-2 inhibitor having a diaryl heterocyclic structure, i.e. a tricyclic structure has been widely studied as a potent candidate. The diaryl heterocyclic structure has a central ring and a sulfonamide or methylsulfone group attached to one of the aryl rings. An initial substance having such diaryl heterocyclic structure is Dup697 [Bioorganic & Medicinal Chemistry Letters, Vol 5, p2123, 1995]. Since then, SC-58635 having a pyrazol ring (Journal of Medicinal Chemistry, Vol 40, p1347, 1997) and MK-966 having a furanone ring (WO 95/00501) were discovered as derivatives of the Dup697.

One selective COX-2 inhibitor, Celecoxib of formula 42 is disclosed in U.S. Pat. No. 5,466,823. The Celecoxib is a substituted pyrazolyl benzenesulfonamide derivative.

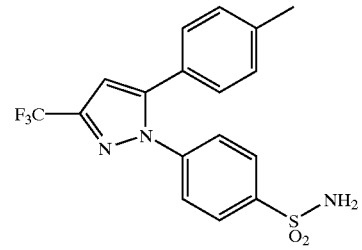

Another selective COX-2 inhibitor, Rofecoxib of formula 43 is disclosed in WO 95/00501. The Rofecoxib has a diaryl heterocyclic structure with a central furanone ring.

Formula 43

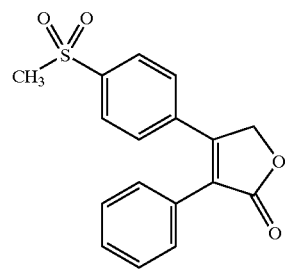

Valdecoxib of formula 44 as another selective COX-2 inhibitor is disclosed in U.S. Pat. No. 5,633,272. The Valdecoxib has a phenylsulfonamide moiety with a central isoxazole ring.

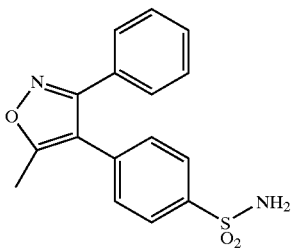

Formula 44

The selective COX-2 inhibitors of formulas 42 to 44 are effective inflammatory therapeutic agents with fewer and less side effects in comparison with conventional nonsteroidal antiinflammatory agents.

SUMMARY OF THE INVENTION

An aspect of the present invention provides a 1,2,4-triazole derivative of formula 1 or a non-toxic salt thereof.

Another aspect of the present invention provides a method for preparing a 1,2,4-triazole derivative or a non-toxic salt thereof.

Another aspect of the present invention provides a pharmaceutical composition comprising a 1,2,4-triazole derivative or a non-toxic salt thereof as an active ingredient for the treatment of fever, pain, and inflammation.

Yet another aspect of the present invention provides a pharmaceutical composition comprising a 1,2,4-triazole derivative or a non-toxic salt thereof as an active ingredient for the treatment of cancers and dementia.

DETAILED DESCRIPTION OF THE INVENTION

According to an aspect of the present invention, there is provided a 1,2,4-triazole derivative represented by formula 1:

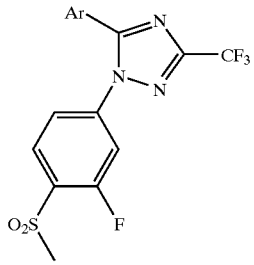

Formula 1 wherein, Ar represents naphthyl; 3,4-methylenedioxyphenyl; phenyl; or phenyl substituted with the group selected from $C_1$–$C_6$ alkyl, $C_1$–$C_6$ alkoxy, or halogen;

or a non-toxic salt thereof.

The 1,2,4-triazole derivative of formula 1 may be present in a form of a non-toxic salt. The term, "non-toxic salt" as used herein refers to a pharmaceutically acceptable, toxin-free salt, including an organic salt and an inorganic salt.

The Inorganic salt of the 1,2,4-triazole derivative of formula 1 includes an inorganic salt of aluminum, ammonium, calcium, copper, iron, lithium, magnesium, manganese, potassium, sodium, or zinc but is not limited thereto. Preferably, an inorganic salt of ammonium, calcium, potassium, or sodium is used.

The organic salt of the 1,2,4-triazole derivative of formula 1 includes an organic amine salt of primary, secondary, or tertiary amine, substituted amine that is present in nature, or cyclic amine, or a salt of a basic ion exchange resin but is not limited thereto. Examples of the salt of a basic ion exchange resin include a salt of arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpyperidine, N-methylglucamine, glutamine, glucosamine, histidine, hydroamine, N-(2-hydroxyethyl) pyperidine, N-(2-hydroxyethyl)pyrrolidine, isopropylamine, lysine, methylglucamine, morpholine, piperazine, piperidine, polyamine resin, procaine, purine, theobromine, triethylamine, trimethylamine, tripropylamine, and tromethamine.

The 1,2,4-triazole derivative of formula 1 may be present in a form of an organic acid salt or an inorganic acid salt.

Examples of the organic acid salt or the inorganic acid salt of the 1,2,4-triazole derivative of formula 1 include a salt of acetic acid, adipic acid, aspartic acid, 1,5-naphthalene disulfonic acid, benzene sulfonic acid, benzoic acid, camphor sulfonic acid, citric acid, 1,2-ethane disulfonic acid, ethane sulfonic acid, ethylenediaminetetraacetic acid, fumaric acid, glucoheptonic acid, gluconic acid, glutamic acid, hydroiodic acid, hydrobromic acid, hydrochloric acid, icethionic acid, lactic acid, maleic acid, malic acid, madelic acid, methane sulfonic acid, mucinic acid, 2-naphthalenedisulfonic acid, nitric acid, oxalic acid, pentothenic acid, phosphoric acid, pivalric acid, propionic acid, salicylic acid, stearic acid, succinic acid, sulfuric acid, tartaric acid, p-toluene sulfonic acid, undecanoic acid, and 10-undecenoic acid. Preferably, a salt of succinic acid, hydrobromic acid, hydrochloric acid, maleic acid, methanesulfonic acid, phosphoric acid, sulfuric acid, or tartaric acid is used.

The 1,2,4-triazole derivative of the present invention preferably includes:

1-(3-fluoro-4-methanesulfonylphenyl)-5-phenyl-3-trifluoromethyl-1H-1,2,4-triazole;

1-(3-fluoro-4-methanesulfonylphenyl)-5-(4-methoxyphenyl)-3-trifluoromethyl-1H-1,2,4-triazole;

1-(3-fluoro-4-methanesulfonylphenyl)-5-(4-fluorophenyl)-3-trifluoromethyl-1H-1,2,4-triazole;

1-(3-fluoro-4-methanesulfonylphenyl)-5-(4-bromophenyl)-3-trifluoromethyl-1H-1,2,4-triazole;

1-(3-fluoro-4-methanesulfonylphenyl)-5-(4-chlorophenyl)-3-trifluoromethyl-1H-1,2,4-triazole;

1-(3-fluoro-4-methanesulfonylphenyl)-5-(4-methylphenyl)-3-trifluoromethyl-1H-1,2,4-triazole;

1-(3-fluoro-4-methanesulfonylphenyl)-5-(4-ethoxyphenyl)-3-trifluoromethyl-1H-1,2,4-triazole;

1-(3-fluoro-4-methanesulfonylphenyl)-5-(3-chlorophenyl)-3-trifluoromethyl-1H-1,2,4-triazole;

1-(3-fluoro-4-methanesulfonylphenyl)-5-(3-fluorophenyl)-3-trifluoromethyl-1H-1,2,4-triazole;

1-(3-fluoro-4-methanesulfonylphenyl)-5-(3-fluoro-4-methoxyphenyl)-3-trifluoromethyl-1H-1,2,4-triazole;

1-(3-fluoro-4-methanesulfonylphenyl)-5-(3-methylphenyl)-3-trifluoromethyl-1H-1,2,4-triazole;

1-(3-fluoro-4-methanesulfonylphenyl)-5-(naphthalene-2-yl)-3-trifluoromethyl-1H-1,2,4-triazole;

5-([1,3])benzodioxole-5-yl)-1-(3-fluoro-4-methanesulfonylphenyl)-3-trifluoromethyl-1H-1,2,4-triazole; and 1-(3-fluoro-4-methanesulfonylphenyl)-5-(3,4-difluorophenyl)-3-trifluoromethyl-1H-1,2,4-triazole.

According to another aspect of the present invention, there is provided an amidrazone derivative as an intermediate for the synthesis of the 1,2,4-triazole derivative of formula 1, as represented by formula 2:

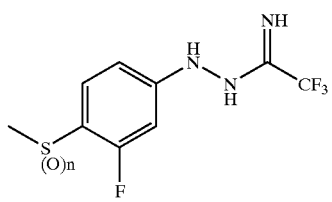

Formula 2 wherein, n is 0 or 2.

According to another aspect of the present invention, there is provided a method for preparing a 1,2,4-triazole derivative of formula 1 or a non-toxic salt thereof, comprising reacting an amidrazone derivative of formula 2a with an acyl chloride of formula 3 in the presence of a

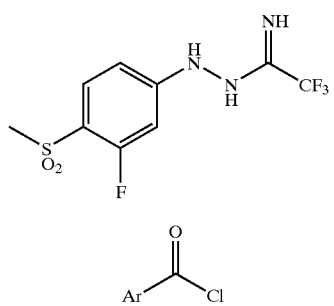

Formula 2a

Formula 3 wherein, Ar is as defined in formula 1.

According to another aspect of the present invention, there is provided a method for preparing a 1,2,4-triazole derivative of formula 1 or a non-toxic salt thereof, comprising reacting an amidrazone derivative of formula 2b with an acyl chloride of formula 3 in the presence of a base and oxidizing the resultant compound.

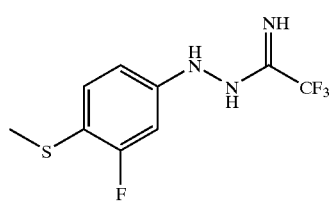

Formula 2b

The aforementioned reactions to form 1,2,4-triazole are preferably carried out in a polar solvent. Examples of the polar solvent include DMF, 1,4-dioxane, DMSO, methylpyrrolidinone, or m-xylene.

The reactions are preferably carried out at the ambient temperature to 110° C. A reaction time is determined depending on the reactants. Generally, the reaction time lasts 5 minutes to 36 hours.

When the reactions are completed, the reaction resultants are extracted by adding water and an organic solvent such as ethyl acetate, dichloromethane, tetrahydrofuran, and ether, to remove salts. The obtained crude extracts are purified by silica gel column chromatography or recrystalization using proper solvent to give final products.

The base may be an organic base or an inorganic base. Among the preferred organic base, preferably triethyl amine trimethyl amine, tripropyl amine, pyridine, or imidazole is used. Among the inorganic base, preferably sodium acetate, sodium hydroxide, sodium hydride, potassium hydroxide, sodium carbonate, or potassium carbonate is used.

The oxidative reaction is preferably carried out in dichloromethane in the presence of an oxidizing agent. Preferably, MMPP (Magnesium monoperoxyphthalate hexahydrate), MCPBA (m-chloroperoxybenzoic acid), or Oxone (potassium peroxymonosulfate) is used as the oxidizing agent.

The compound of formula 2 may be prepared by reacting a hydrazine derivative of formula 4 with a trifluoroacetimidine of formula 5 in the presence of a base.

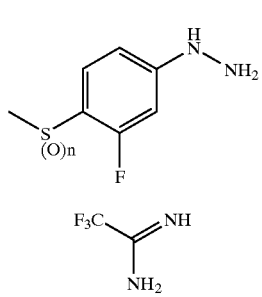

Formula 4

Formula 5 wherein, n is 0 or 2.

The aforementioned reactions are preferably carried out in a mixed solvent of THF with methanol or ethanol.

The reactions are preferably carried out at an ambient temperature to 66° C. A reaction time is determined depending on the reactants. Generally, the reaction time lasts 10 minutes to 24 hours.

When the reactions are completed, the reaction resultants are washed with water and an organic solvent such as ethyl acetate, dichloromethane, tetrahydrofuran, and ether, to remove salts. The obtained crude extracts are purified by silica gel column chromatography to give final products.

The base may be an organic base or an inorganic base. Among the preferred organic base, preferably triethyl amine, trimethyl amine, tripropyl amine, pyridine, or imidazole is used. Among the inorganic base, preferably sodium acetate, sodium hydroxide, sodium hydride, potassium hydroxide, sodium carbonate, or potassium carbonate is used.

When all the said reactions are finished, separation and purification of the reaction products can be performed by chromatography, recrystallization, or any other processes, which are conventionally used in the relevant field.

The method for preparing a compound of formula 1 can be expressed serially by the following reaction formula 1.

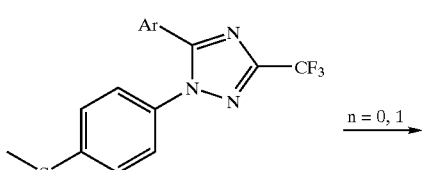

Reaction Formula 1

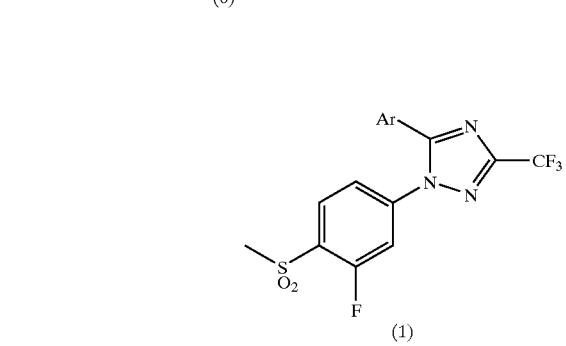

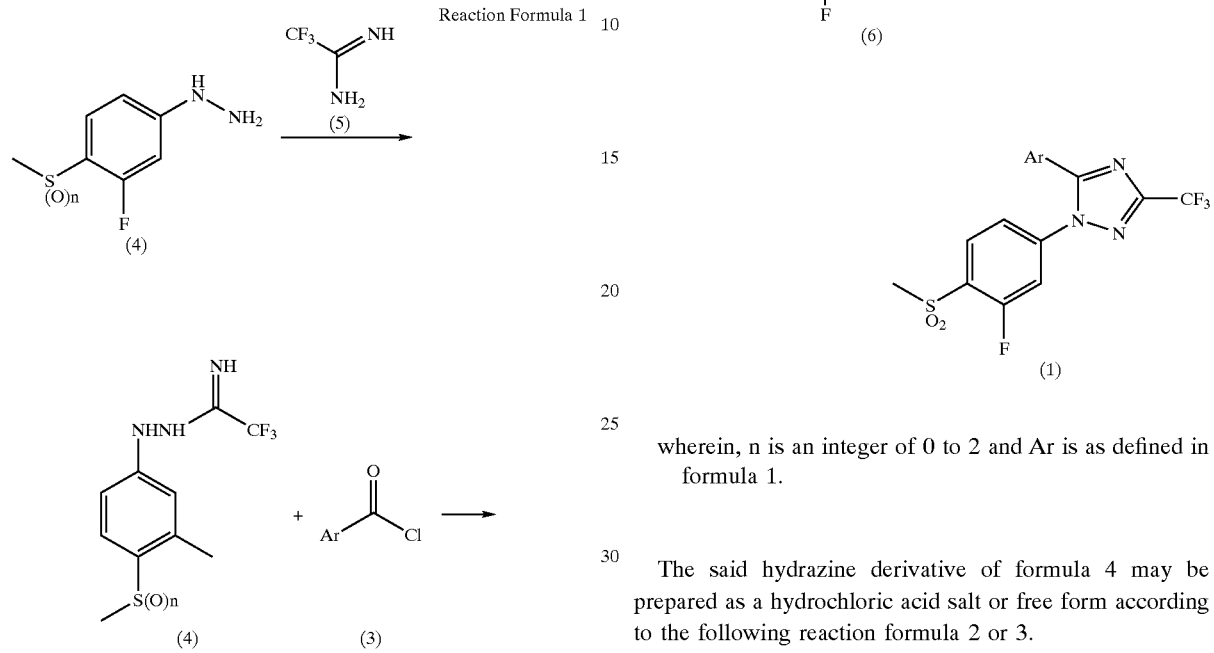

wherein, n is an integer of 0 to 2 and Ar is as defined in formula 1.

The said hydrazine derivative of formula 4 may be prepared as a hydrochloric acid salt or free form according to the following reaction formula 2 or 3.

Reaction formula 2

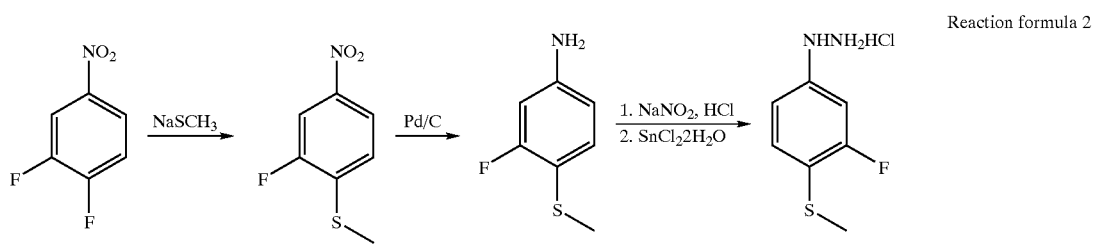

Reaction formula 3

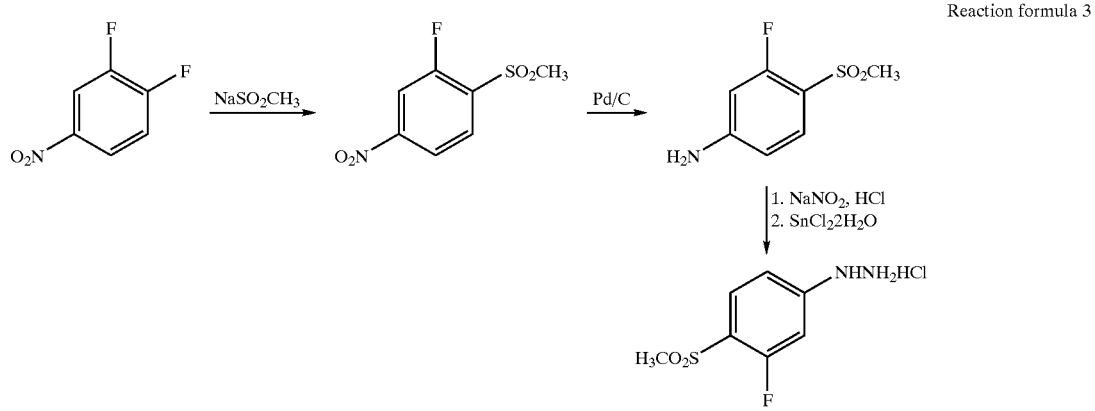

In the reaction formula 2, 2-fluoro-1-methylsulfanyl-4-nitrobenzene is prepared by reacting 1,2-difluoro-4-nitrobenzene and sodium thiomethoxide. The reactions are preferably carried out in a conventionally used nonpolar solvent such as NMP, DMF, DMSO, THF, or a mixture thereof. More preferably, DMF/THF (1/10) is used. The said reactions are preferably carried out at an ambient temperature to the the boiling point. If the reaction is done at the boiling point, the reactants may be refluxed.

In the reaction formula 3, 2-fluoro-1-methanesulfonyl4-nitrobenzene is prepared by reacting 1,2-difluoro-4-nitrobenzene and sodium methanesulfinate. The said reactions are preferably carried out in a conventionally used nonpolar solvents such as NMP, DMF, DMSO, THF, or a mixture thereof. More preferably, DMF/THF (1/10) is used. The said reactions are preferably carried out at an ambient temperature to the the boiling point. If the reaction is done at the boiling point, the reactatnts may be refluxed.

In the reaction formula 2 and 3, the reduction reaction of the nitrobenzene may be carried out using sodium borohydride/nickel chloride six hydrate, Pd/C, Fe, etc. which are conventionally used in the relevant field.

In the reaction formula 2 and 3, benzenehydrazine may be prepared using the method disclosed in EP 1104760A1.

The reaction conditions such as reaction solvent, base, and the amount of reactant, are not necessarily limited as described above, and may be modified by combining many methods disclosed in publications in the relevant field.

According to another aspect of the present invention, there is provided a pharmaceutical composition comprising a therapeutically effective amount of a 1,2,4-triazole derivative of formula 1 or a non-toxic salt thereof as an active ingredient and a pharmaceutically acceptable carrier for the treatment of fever, pain, and inflammation.

The pharmaceutical composition comprises a compound of formula 1 or a non-toxic salt thereof when it is a selective inhibitor of cyclooxygenase-2. Therefore, the pharmaceutical composition can be used as an antipyretic, an analgesic, and an antiinflammatory agent, with reduced side effects.

Conventional nonsteroidal antiinflammatory agents non-selectively inhibit the prostaglandin synthesis enzymes, cyclooxygenase-1 and cyclooxygenase-2. Therefore, various side effects may occur.

On the other hand, a compound of formula 1 and a non-toxic salt thereof selectively inhibit cyclooxygenase-2. Therefore, the side effects of conventional nonsteroidal antipyretics, analgesics, and antiinflammatory agents can be reduced.

The pharmaceutical composition of the present invention comprises a compound of formula 1 and/or a non-toxic salt thereof and a pharmaceutically acceptable carrier or excipient. Therefore, the pharmaceutical composition may be used as a substitute for conventional nonsteroidal antiinflammatory agents. In particular, due to the reduction of the side effects of conventional nonsteroidal antipyretics, analgesics, and antiinflammatory agents, the pharmaceutical composition of the present invention is useful for treating patients with peptic ulcer, gastritis, regional enteritis, ulcerative colitis, diverticullitis, gastrorrhagia, or hypoprothrombinemia.

The pharmaceutical composition of the present invention can be used in all inflammatory diseases associated with pathological prostaglandin and is particularly useful in treating osteoarthritis and rheumatoid arthritis, which require high dosage of nonsteroidal antiinflammatory agents.

The pharmaceutical composition of the present invention can be administered in form of an adult dosage of 1 mg/day to 1000 mg/day of the compound of formula 1. An adequate dosage is determined depending on the degree of disease severity.

According to yet another aspect of the present invention, there is provided a pharmaceutical composition comprising a therapeutically effective amount of a 1,2,4-triazole derivative of formula 1 or a non-toxic salt thereof and a pharmaceutically acceptable carrier for the treatment of cancers and dementia.

Recently, it was reported that nonsteroidal antiinflammatory agents are effective in the treatment of large intestine cancer [European Journal of Cancer, Vol 37, p2302, 2001], prostate cancer [Urology, Vol 58, p127, 2001], and dementia [Exp. Opin. Invest. Drugs, Vol 9, p671, 2000]. Therefore, it is understood that the pharmaceutical composition of the present invention as a nonsteroidal antiinflammatory agent can also be used for the treatment of these diseases.

The pharmaceutical composition of the present invention can be administered in the form of an adult dosage of 1 mg/day to 1000 mg/day of the compound of formula 1 or a non-toxic salt thereof. An adequate dosage is determined depending on the degree of disease severity.

The pharmaceutical composition of the present invention may be administered in the form of tablet, foam tablet, capsule, granule, powder, sustained-release tablet, sustained-release capsule (a single unit formulation or a multiple unit formulation), intravenous and intramuscularly injectable solution, infusion solution, suspension, or suppository, or in other suitable dosage forms.

Sustained-release pharmaceutical dosage forms contain active ingredients with or without an initial loading dose. They are wholly or partially sustained-release pharmaceutical dosage forms to release active ingredients in a controlled manner.

Preferably, the pharmaceutical composition is orally administered.

The pharmaceutical composition further comprises a pharmaceutically acceptable excipient and/or diluent and/or adjuvant in pharmaceutically effective amounts.

Examples of the excipient and adjuvant include gellatin, a natural sugar such as sucrose and lactose, lecitin, pectin, starch such as corn starch and amylose, cyclodextrin and cyclodextrin derivative, dextran, polyvinylpyrrolidone, polyvinyl acetate, Arabic gum, arginic acid, xylose, talc, salicylic acid, calcium hydrogen phosphate, cellulose, cellulose derivative such as methylcellulose, methoxypropyl cellulose, hydroxypropylmethyl cellulose, and hydroxypropylmethylcellulose phthalate, fatty acid having 12 to 22 carbon atoms, emulsifying agent, oil and fat, in particular, vegetable glycerol ester and polyglycerol ester of saturated fatty acids, monohydric alcohol, polyhydric alcohol, polyglycol such as polyethylene glycol, aliphatic alcohol having 1 to 20 carbon atoms, or aliphatic saturated or unsaturated fatty acid ester having 2 to 22 carbon atoms with polyhydric alcohols such as glycol, glycerol, diethylene glycol, 1,2-propylene glycol, sorbitol, and mannitol.

Other suitable adjuvants include a disintegrating agent. Examples of the disintegrating agent include a cross-linked polyvinylpyrrolidone, sodium carboxymethyl starch, sodium carboxymethyl cellulose, and microcrystalline cellulose. A coating agent which is conventionally used in this field may also be used. Examples of the coating agent include acrylic acid and/or methacrylic acid and/or an ester polymer or copolymer thereof, zein, ethyl cellulose, ethyl cellulose succinate, and Shellac.

A plasticizer suitable for the coating agent is citric ester and tartaric ester, glycerol and glycerol ester, or polyethylene glycol with different chain lengths.

A liquid composition such as solution and suspension is formulated in water or a physiological acceptable organic solvent such as alcohol and aliphatic alcohol.

The liquid pharmaceutical composition may further comprise a preservative such as potassium solvate, methyl 4-hydroxybenzoate, and propyl 4-hydroxybenzoate, an antioxidant such as ascorbic acid, and a fragrant such as peppermint oil.

In addition, when the liquid pharmaceutical composition is formulated, a conventional solubilizer or emulsifier such as polyvinylpyrrolidone and polysolvate 80 may be used.

Other examples of suitable excipients and adjuvants are disclosed in Dr. H. P. Fielder, "Lexikon der Hilfsstoffe fur Pharmazie, Kosmetik und angrenzende Gebiete" [Encyclopaedia of auxiliaries for pharmacy, cosmetics and related fields].

Hereinafter, the present invention will be described more specifically by examples. However, the following examples are provided only for illustration and thus the present invention is not limited to or by them.

EXAMPLE 1

3-fluoro-4-methylsulfanylnitrobenzene

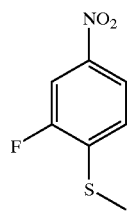

Formula 7

8 g of 3,4-difluoronitrobenzene was dissolved in 50 ml of THF and 5 g of sodium thiomehtoxide was added thereto and stirred for ten minutes, and then 5 ml of DMF was slowly added thereto and stirred at an ambient temperature for 6 hours. The reaction mixture was diluted with 200 ml of water to obtain light yellow solid, which was filtered and washed with cool ethanol and water to give 10.0 g of the title compound as a light yellow solid (yield 88%).

$^1$H-NMR (400 MHz, CDCl$_3$) δ 2.50 (s, 3 H), 7.29 (td, 1 H, 7.5, 8.6 Hz), 7.87 (dd, 1H, J=9.8, 2.3 Hz), 8.12 (ddd, 1 H, J=8.6, 2.3, 0.7 Hz)

EXAMPLE 2

3-fluoro-4-methylsulfanylphenylamine

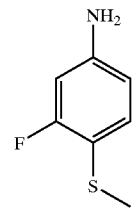

Formula 8

10.0 g of 3-fluoro-4-methylsulfanylnitrobenzene prepared in the above example 1, 0.1 eq of Pd/C (5 wt %), 4 eq of amonium formate were dissolved in THF/MeOH (1:1) and refluxed for 3 hours. The solid, which was not dissolved in the solution, was filtered away, and the filtrate was distilled under reduced pressure to obtain oily compound, which was dissolved again in 80 ml of ethyl acetate. Solid amonium formate which was not dissolved in the solution, was filtered away, and the filtrate was distilled under reduced pressure to obtain oily filtrate, which was purified by column chromatography (ethyl acetate:n-Hexane=1:3) to give 6.04 g of the title compound as a yellow solid (yield 88%).

$^1$H-NMR (400 MHz, CDCl$_3$) δ 3.01 (s, 3 H), 6.59 (td, 1 H, 7.5, 8.6 Hz), 6.72 (dd, 1 H, J=9.8, 2.3 Hz), 7.54 (ddd, 1 H, J=8.6, 2.3, 0.7 Hz)

EXAMPLE 3

3-fluoro-4-methylsulfanylphenyhydrazine hydrocholride

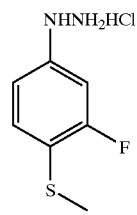

Formula 9

3.8 g of 3-fluoro-4-methylsulfanylphenylamine prepared in the above example 2, was dissolved in 30 ml of conc. HCl at −10° C., and 1.5 eq of sodium nitrite in 20 ml of water was slowly added thereto and stirred for 2 hours at the same temperature, and then 3 eq of tin chloride dihydrate in 30 ml of conc. HCl was slowyl added thereto and stirred for 1 hour at the same temperature and 10 hours at an ambient temperature, the reaction progress of which was identified by using TLC (ethyl acetate:n-hexane=1:3). When the reaction was completed, the reaction mixture was adjusted to pH 9 with sodium hydroxide solution, and stirred for 30 minutes, and 200 ml of THF was added thereto and stirred for 30 minutes again. The reaction mixture was filtered, and the filtrate was to extracted three times with 200 ml of water and THF. The THF layer was dried on anhydrous magnesium sulfate and distilled under reduced pressure to obtain oily filtrate, which was followed by the dissolution with 10 ml of ethyl acetate. Then 2 ml of 4N hydrochloric acid in dioxane was added to the solution and the solution was distilled under reduced pressure. 100 ml of isopropyl alcohol

EXAMPLE 4

N-(3-fluoro-4-methylsulfanylphenyl) trifluoroacetamidrazone

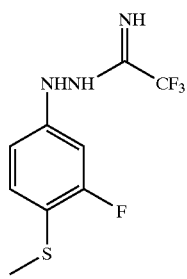

Formula 10

900 mg of 3-fluoro-4-methylsulfanylphenyl hydrazine hyrdrochloride prepared in the above example 3, was dissolved in 40 ml of mixed solution (MeOH: THF=1:1), 0.80 ml of triethylamine was added dropwise thereto, and the reaction mixture was stirred for 30 minutes. Then 910 mg of trifluoroacetimidine (85%) was added dropwise thereto and stirred for 24 hours at an ambient temperature. When the reaction was completed, water and ethyl acetate was added thereto, the water layer was extracted with ethyl acetate two times, and then the organic layer was washed with saturated sodium chloride solution once and was dried on anhydrous magnesium sulfate and filtered under reduced pressure. The resultant was purified by column chromatography (ethyl acetate:n-hexane=1:4) to give 700 mg of the title compound as a liquid (yield 67%).

$^1$H-NMR (400 MHz, DMSO-d6) δ 2.40 (s, 3 H), 6.50 (s, 2 H), 6.60–6.70 (m, 1 H), 7.25 (t, 2 H, J=8.4 Hz), 8.75 (s, 1 H)

EXAMPLE 5

3-fluoro-4-methanesulfonylnitrobenzene

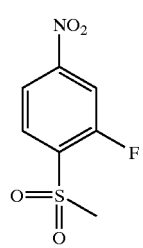

Formula 11

8 g of 3,4-difluoronitrobenzene and 1.01 eq of sodium methanesulfinate (95%) was dissolved in 10 ml of DMSO. The solution was stirred at 60° C. for 3 hours. When the reaction was completed, the solution was added to 100 ml of water to form pale yellow solid, followed by filtration and washing with 50 ml of cool water and 30 ml of n-hexane separately to give 8.8 g of the title compound as a pale yellow solid (yield 79%).

Mass (Low El)=219.0 was slowyl added thereto to form a solid product, followed by a filtration to give 2.30 g of the title compound as a pale yellow solid (yield 62%).

EXAMPLE 6

3-fluoro-4-methanesulfonylphenylamine

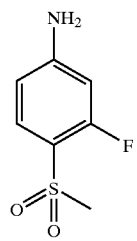

Formula 12

6.04 g (yield 70%) of the title compound as a liquid was prepared in the same manner as in Example 2 except using 10.0 g of 3-fluoro-4-methanesulfonylnitrobenzene instead of 3-fluoro-4-methylsulfanylnitrobenzene.

Mass (Low El)=184.1(M+)

EXAMPLE 7

3-fluoro-4-methanesulfonylphenylhydrazine hydrochloride

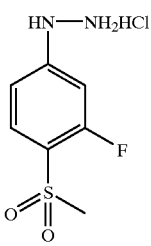

Formula 13

2.30 g (yield 62%) of the title compound as a solid was prepared in the same manner as in Example 3 except using 3.5 g of 3-fluoro-4-methanesulfonylphenylamine instead of 3-fluoro-4-methylsulfanylphenylamine.

EXAMPLE 8

N-(3-fluoro-4-methanesulfonylphenyl) trifluoroacetamidrazone

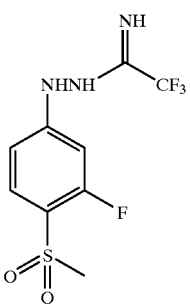

Formula 14

340 mg (yield 34%) of the title compound as a solid was prepared in the same manner as in Example 4 except using 900 mg of 3-fluoro-4-methanesulfonylphenylhydrazine hydrochloride instead of 3-fluoro-4-methylsulfanylphenylhydrazine hydrochloride.

$^1$H-NMR (400 MHz, DMSO-d6) δ 3.12 (s, 3 H), 6.85–7.00 (m, 3 H), 7.75 (t, 2 H, J=8.5 Hz), 9.35 (s, 1 H)

EXAMPLE 9

1-(3-fluoro-4-methylsulfanylphenyl)-5-phenyl-3-trifluoromethyl-1H-1,2,4-triazole

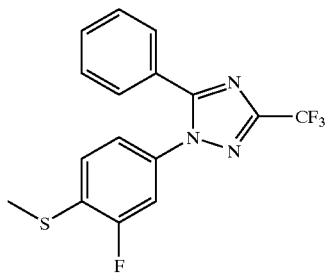

Formula 15

200 mg of N-(3-fluoro-4-methylsulfanylphenyl)trifluoroacetamidrazone was dissolved in 5 ml of 1,4-dioxane, and 0.06 ml of pyridine was added dropwise thereto. The reaction mixture was stirred at an ambient temperature for 10 minutes and then 110 mg of benzoyl chloride was added thereto. The reaction mixture was refluxed at its boiling point for 12 hours. When the reaction was completed, the reaction mixture was cooled to an ambient temperature and then water and ethyl acetate were added thereto. The water layer was extracted with ethyl acetate two times, and then the obtained organic layer was washed with saturated sodium chloride solution once, dried over on anhydrous magnesium sulfate, and filtered under reduced pressure. The resultant was purified by column chromatography (ethyl acetate:n-hexane=1;4) to give 170 mg of the title compound as a liquid (yield 65%).

EXAMPLE 10

1-(3-fluoro-4-methylsulfanylphenyl)-5-(4-methoxyphenyl)-3-trifluoromethyl-1H-1,2,4-triazole

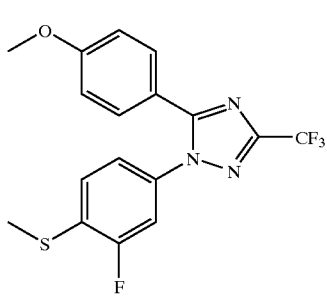

Formula 16

200 mg (yield 70%) of the title compound as a liquid was prepared in the same manner as in Example 9 except using 120 mg of 4-methoxybenzoylchloride instead of benzoylchloride.

EXAMPLE 11

1-(3-fluoro-4-methylsulfanylphenyl)-5-(4-fluorophenyl)-3-trifluoromethyl-1H-1,2,4-triazole

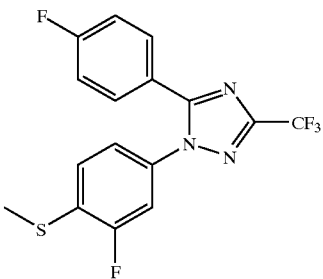

Formula 17

166 mg (yield 60%) of the title compound as a liquid was prepared in the same manner as in Example 9 except using 120 mg of 4-fluorobenzoylchloride instead of benzoylchloride.

EXAMPLE 12

1-(3-fluoro-4-methylsulfanylphenyl)-5-(4-bromophenyl)-3-trifluoromethyl-1H-1,2,4-triazole

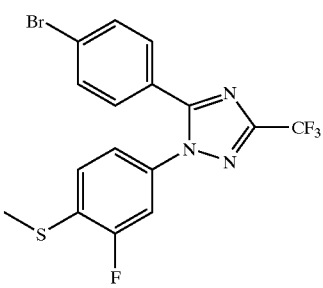

Formula 18

209 mg (yield 65%) of the title compound as a liquid was prepared in the same manner as in Example 9 except using 130 mg of 0.4-bromobenzoylchloride instead of benzoylchloride.

EXAMPLE 13

1-(3-fluoro-4-methylsulfanylphenyl)-5-(4-chlorophenyl)-3-trifluoromethyl-1H-1,2,4-triazole

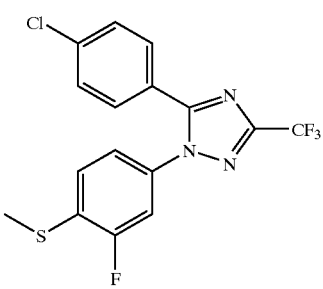

Formula 19

200 mg (yield 68%) of the title compound as a liquid was prepared in the same manner as in Example 9 except using 120 mg of 4-chlorobenzoylchloride instead of benzoylchloride.

EXAMPLE 14

1-(3-fluoro-4-methylsulfanylphenyl)-5-(4-methylphenyl)-3-trifluoromethyl-1H-1,2,4-triazole Formula 20

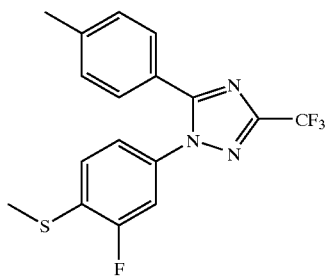

158 mg (yield 58%) of the title compound as a liquid was prepared in the same manner as in Example 9 except using 125 mg of 4-methylbenzoylchloride instead of benzoylchloride.

EXAMPLE 15

1-(3-fluoro-4-methylsulfanylphenyl)-5-(4-ethoxyphenyl)-3-trifluoromethyl-1H-1,2,4-triazole Formula 21

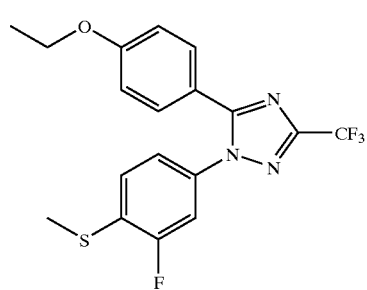

196 mg (yield 66%) of the title compound as a liquid was prepared in the same manner as in Example 9 except using 115 mg of 4-ethoxybenzoylchloride instead of benzoylchloride.

EXAMPLE 16

1-(3-fluoro-4-methylsulfanylphenyl)-5-(3-chlorophenyl)-3-trifluoromethyl-1H-1,2,4-triazole Formula 22

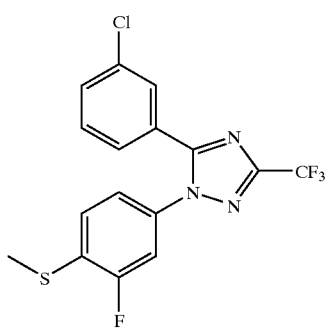

192 mg (yield 66%) of the title compound as a liquid was prepared in the same manner as in Example 9 except using 115 mg of 3-chlorobenzoylchloride instead of benzoylchloride.

EXAMPLE 17

1-(3-fluoro-4-methylsulfanylphenyl)-5-(3-fluorophenyl)-3-trifluoromethyl-1H-1,2,4-triazole Formula 23

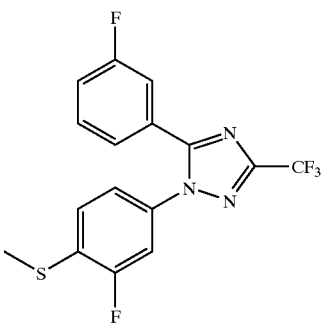

189 mg (yield 68%) of the title compound as a liquid was prepared in the same manner as in Example 9 except using 110 mg of 3-fluorobenzoylchloride instead of benzoylchloride.

EXAMPLE 18

1-(3-fluoro-4-methylsulfanylphenyl)-5-(3-fluoro-4-methoxyphenyl)-3-trifluoromethyl-1H-1,2,4-triazole Formula 24

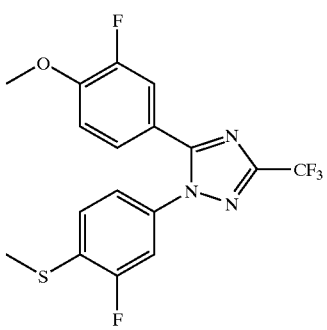

181 mg (yield 61%) of the title compound as a liquid was prepared in the same manner as in Example 9 except using 120 mg of 3-fluoro-4-methoxybenzoylchloride instead of benzoylchloride.

EXAMPLE 19

1-(3-fluoro-4-methylsulfanylphenyl)-5-(3-methylphenyl)-3-trifluoromethyl-1H-1,2,4-triazole Formula 25

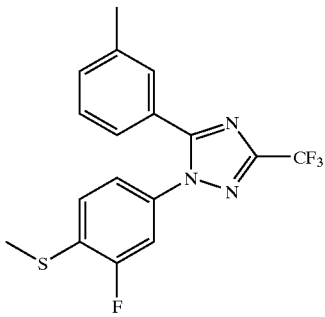

185 mg (yield 71%) of the title compound as a liquid was prepared in the same manner as in Example 9 except using 115 mg of 3-methylbenzoylchloride instead of benzoylchloride.

EXAMPLE 20

1-(3-fluoro-4-methylsulfanylphenyl)-5-(naphthalene-2-yl)-3-trifluoromethyl-1H-1,2,4-triazole Formula 26

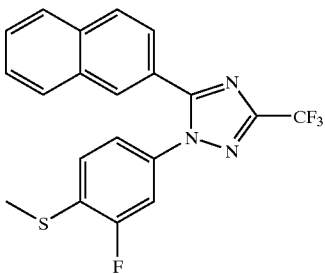

196 mg (yield 65%) of the title compound as a liquid was prepared in the same manner as in Example 9 except using 140 mg of naphthalene-2-carbonylchloride instead of benzoylchloride.

EXAMPLE 21

5-([1,3]benzodioxole-5-yl-1-(3-fluoro-4-methylsulfanylphenyl)-3-trifluoromethyl-1H-1,2,4-triazole Formula 27

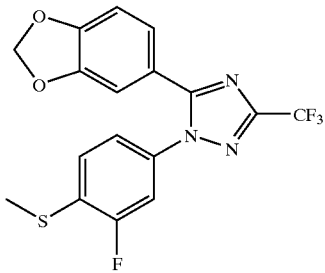

172 mg (yield 58%) of the title compound as a liquid was prepared in the same manner as in Example 9 except using 140 mg of [1,3]benzodioxole-5-carbonylchloride instead of benzoylchloride.

EXAMPLE 22

1-(3-fluoro-4-methanesulfonylphenyl)-5-phenyl-3-trifluoromethyl-1H-1,2,4-triazole Formula 28

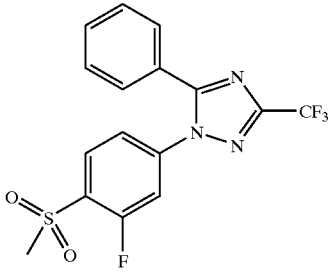

150 mg of 1-(3-fluoro-4-methylsulfanylphenyl)-5-phenyl-3-trifluoromethyl-1H-1,2,4-triazole prepared in the above example 9 was dissolved in the mixed sovent (5 ml of dichloromethane, 1 ml of methanol), and 350 mg of MMPP was slowly added thereto. The reaction mixture was stirred for 5 hours and was filtered, and the filtrate was washed with sodium bicarbonate and saturated sodium chloride solution separately once and dried over anhydrous magnesium sulfate and then filtered under reduced pressure. The resultant was purified by column chromatography (ethyl acetate:n-hexane=2:3) to give 139 mg of the title compound as a solid (yield 88%).

$^1$H NMR (400 MHz, CDCl$_3$) δ 3.20 (s, 3 H), 7.20–7.50 (m, 6H), 8.05 (m, 1H), 8.15 (m, 1H)

EXAMPLE 23

1-(3-fluoro-4-methanesulfonylphenyl)-5-(4-methoxyphenyl)-3-trifluoromethyl-1H-1,2,4-triazole Formula 29

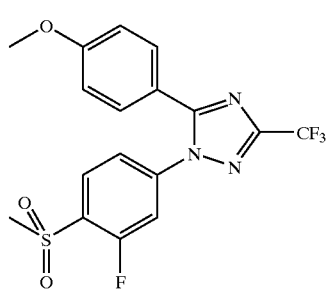

90 mg (yield 70%) of the title compound as a liquid was prepared in the same manner as in Example 22 except using 120 mg of 1-(3-fluoro-4-methylsulfanylphenyl)-5-(4-methoxyphenyl)-3-trifluoromethyl-1H-1,2,4-triazole prepared in the example 10 instead of 1-(3-fluoro-4-methylsulfanylphenyl)-5-phenyl-3-trifluoromethyl-1H-1,2,4-triazole.

$^1$H NMR (400 MHz, CDCl$_3$) δ 3.20 (s, 3 H), 3.90 (s, 3 H), 6.80 (d, 2 H, J=8.4 Hz), 7.35 (m, 1H), 7.45 (d, 2 H, J=8.4 Hz), 8.05 (m, 1 H), 0.15 (m, 1H)

EXAMPLE 24

1-(3-fluoro-4-methanesulfonylphenyl)-5-(4-fluorophenyl)-3-trifluoromethyl-1H-1,2,4-triazole

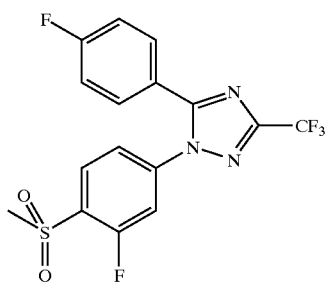

Formula 30

125 mg (yield 77%) of the title compound as a liquid was prepared in the same manner as in Example 22 except using 150 mg of 1-(3-fluoro-4-methylsulfanylphenyl)-5-(4-fluorophenyl)-3-trifluoromethyl-1H-1,2,4-triazole prepared in the example 11 instead of 1-(3-fluoro-4-methylsulfanylphenyl)-5-phenyl-3-trifluoromethyl-1H-1,2,4-triazole.

$^1$H NMR (400 MHz, CDCl$_3$) δ 3.20 (s, 3 H), 7.00 (dd, 2 H, J=8.5, 8.7 Hz), 7.30–7.36 (m, 1 H), 7.45 (dd, 1 H, J=2.0, 9.7 Hz), 7.50–7.60 (m, 2 H), 8.05 (dd, 1 H, J=7.4, 8.4 Hz)

EXAMPLE 25

1-(3-fluoro-4-methanesulfonylphenyl)-5-(4-bromophenyl)-3-trifluoromethyl-1H-1,2,4-triazole

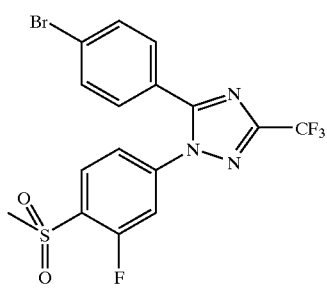

Formula 31

142 mg (yield 88%) of the title compound as a solid was prepared in the same manner as in Example 22 except using 150 mg of 1-(3-fluoro-4-methylsulfanylphenyl)-5-(4-bromophenyl)-3-trifluoromethyl-1H-1,2,4-triazole prepared in the example 12 instead of 1-(3-fluoro-4-methylsulfanylphenyl)-5-phenyl-3-trifluoromethyl-1H-1,2,4-triazole.

$^1$H NMR (400 MHz, CDCl$_3$) δ 3.20 (s, 3 H), 7.20 (dd, 1 H, J=7.0, 1.9 Hz), 7.40 (d, 2 H, J=6.9 Hz), 7.50–7.65 (m, 3 H), 8.05 (dd, 1 H, J=7.4, 8.4 Hz)

EXAMPLE 26

1-(3-fluoro-4-methanesulfonylphenyl)-5-(4-chlorophenyl-3-trifluoromethyl-1H-1,2,4-triazole

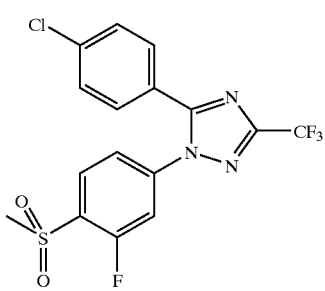

Formula 32

113 mg (yield 87%) of the title compound as a liquid was prepared in the same manner as in Example 22 except using 120 mg of is 1-(3-fluoro-4-methylsulfanylphenyl)-5-(4-chlorophenyl)-3-trifluoromethyl-1 H-1,2,4-triazole prepared in the example 13 instead of 1-(3-fluoro-4-methylsulfanylphenyl)-5-phenyl-3-trifluoromethyl-1H-1,2,4-triazole.

$^1$H NMR (400 MHz, CDCl$_3$) δ 3.20 (s, 3 H), 7.20 (d, 1 H, J=8.0 Hz), 7.40–7.60 (m, 5 H), 8.00 (dd, 1 H, J=8.5, 8.5 Hz)

EXAMPLE 27

1-(3-fluoro-4-methanesulfonylphenyl)-5-(4-methylphenyl)-3-trifluoromethyl-1H-1,2,4-triazole

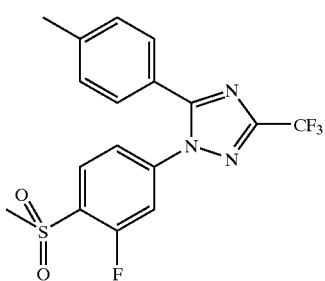

Formula 33

100 mg (yield 77%) of the title compound as a solid was prepared in the same manner as in Example 22 except using 120 mg of 1-(3-fluoro-4-methylsulfanylphenyl)-5-(4-methylphenyl)-3-trifluoromethyl-1H-1,2,4-triazole prepared in the example 14 instead of 1-(3-fluoro-4-methylsulfanylphenyl)-5-phenyl-3-trifluoromethyl-1H-1,2,4-triazole.

$^1$H NMR (400 MHz, CDCl$_3$) δ 2.30 (s, 3 H), 3.20 (s, 3 H), 7.10–7.20 (m, 3 H), 7.40–7.55 (m, 3 H), 8.00 (dd, 1 H, J=8.5, 8.5 Hz)

EXAMPLE 28

1-(3-fluoro-4-methanesulfonylphenyl)-5-(4-ethoxyphenyl)-3-trifluoromethyl-1H-1,2,4-triazole

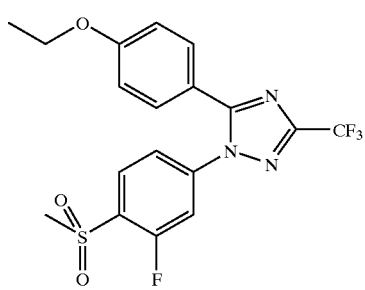

Formula 34

86 mg (yield 80%) of the title compound as a liquid was prepared in the same manner as in Example 22 except using 100 mg of 1-(3-fluoro-4-methylsulfanylphenyl)-5-(4-ethoxyphenyl)-3-trifluoromethyl-1H-1,2,4-triazole prepared in the example 15 instead of 1-(3-fluoro-4-methylsulfanylphenyl)-5-phenyl-3-trifluoromethyl-1H-1,2,4-triazole.

$^1$H NMR (400 MHz, CDCl$_3$) δ 1.50 (t, 3 H, J=6.9 Hz), 3.20 (s, 3 H), 4.10 (q, 2 H, J=6.9 Hz), 6.80 (d, 2 H, J=9.6 Hz), 7.25 (dd, 1 H, J 2.0, 0.7 Hz), 7.40 (dd, 1 H, J=2.0, 7.0 Hz), 7.90 (dd, 1 H, J=7.08.5 Hz), 8.10 (d, 2 H, J=9.6 Hz)

EXAMPLE 29

1-(3-fluoro-4-methanesulfonylphenyl)-5-(3-chlorophenyl)-3-trifluoro methyl-1H-1,2,4-triazole

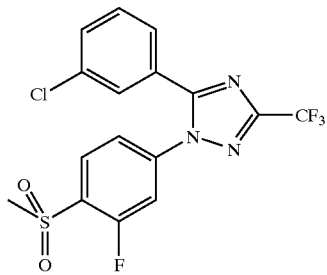

Formula 35

110 mg (yield 84%) of the title compound as a liquid was prepared in the same manner as in Example 22 except using 120 mg of 1-(3-fluoro-4-methylsulfanylphenyl)-5-(3-chlorophenyl)-3-trifluoromethyl-1 H-1,2,4-triazole prepared in the example 16 instead of 1-(3-fluoro-4-methylsulfanylphenyl)-5-phenyl-3-trifluoromethyl-1H-1,2,4-triazole.

$^1$H NMR (400 MHz, CDCl$_3$) δ 3.20 (s, 3 H), 7.00–7.55 (m, 5 H), 8.00 (m, 1 H), 8.05 (m, 1 H)

EXAMPLE 30

1-(3-fluoro-4-methanesulfonylphenyl)-5-(3-fluorophenyl)-3-trifluoro methyl-1H-1,2,4-triazole

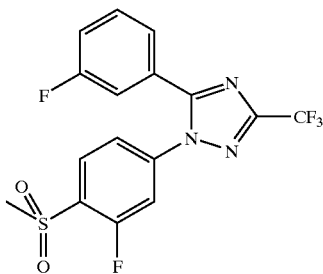

Formula 36

125 mg (yield 77%) of the title compound as a liquid was prepared in the same manner as in Example 22 except using 150 mg of 1-(3-fluoro-4-methylsulfanylphenyl)-5-(3-fluorophenyl)-3-trifluoromethyl-1H-1,2,4-triazole prepared in the example 17 instead of 1-(3-fluoro-4-methylsulfanylphenyl)-6-phenyl-3-trifluoromethyl-1H-1,2,4-triazole.

$^1$H NMR (400 MHz, CDCl$_3$)δ3.20 (s, 3 H), 7.10–7.55 (m, 5 H), 8.05 (m, 1 H), 8.15 (m, 1 H)

EXAMPLE 31

1-(3-fluoro-4-methanesulfonylphenyl)-5-(3-fluoro-4-methoxyphenyl)-3-trifluoromethyl-1H-1,2,4-triazole

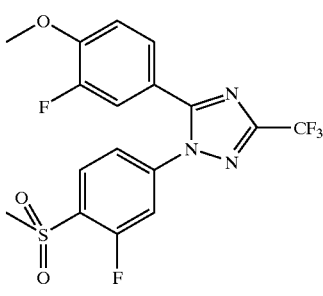

Formula 37

125 mg (yield 77%) of the title compound as a liquid was prepared in the same manner as in Example 22 except using 120 mg of 1-(3-fluoro-4-methylsulfanylphenyl)-5-(3-fluoro-4-methoxyphenyl)-3-trifluoromethyl-1H-1,2,4-triazole prepared in the example 18 instead of 1-(3-fluoro-4-methylsulfanylphenyl)-5-phenyl-3-trifluoromethyl-1H-1,2,4-triazole.

$^1$H NMR (400 MHZ, CDCl$_3$) δ 3.20(s, 3 H), 3.80 (s, 3 H) 7.15–22(m, 2 H), 7.30 (dd, 1 H, J 1.8, 12.9 Hz), 7.35 (m, 1H), 8.05 (m, 1H), 8.15 (m, 1H)

EXAMPLE 32

1-(3-fluoro-4-methanesulfonylphenyl)-5-(3-methylphenyl)-3-trifluoromethyl-1H-1,2,4-triazole

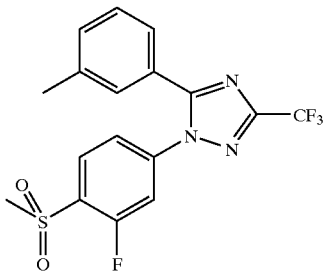

Formula 38

96 mg (yield 75%) of the title compound as a liquid was prepared in the same manner as in Example 22 except using 120 mg of 1-(3-fluoro-4-methylsulfanylphenyl)-5-(3-methylphenyl)-3-trifluoromethyl-1H-1,2,4-triazole prepared in the example 19 instead of 1-(3-fluoro-4-methylsulfanylphenyl)-5-phenyl-3-trifluoromethyl-1H-1,2,4-triazole.

$^1$H NMR (400 MHz, CDCl$_3$) δ 2.30(s, 3 H), 3.30 (s, 3 H), 7.10–7.60 (m, 6 H), 8.00 (dd, 1 H, J=8.5, 8.5 Hz)

EXAMPLE 33

1-(3-fluoro-4-methanesulfonylphenyl)-5-(naphthalene-2-yl)-3-trifluoromethyl-1H-1,2,4-triazole

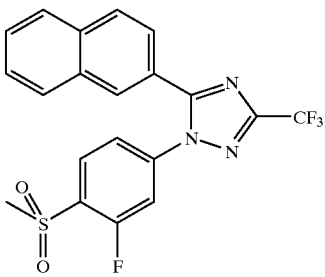

Formula 39

125 mg (yield 77%) of the title compound as a liquid was prepared in the same manner as in Example 22 except using 120 mg of 1-(3-fluoro-4-methylsulfanylphenyl)-5-(naphthalene-2-yl)-3-trifluoromethyl-1H-1,2,4-triazole prepared in the example 20 instead of 1-(3-fluoro-4-methylsulfanylphenyl)-5-phenyl-3-trifluoromethyl-1H-1,2,4-triazole.

$^1$H NMR (400 MHz, CDCl$_3$) δ 3.20 (s, 3 H), 7.35 (ddd, 1 H, J=7.0, 1.9, 0.7 Hz), 7.40 (dd, 1 H, J=8.7, 1.8 Hz), 7.50 (dd, 1 H, J=9.7, 1.8 Hz), 7.55–7.65 (m, 2 H), 7.85–7.95 (m, 3 H), 8.05 (dd, 1 H, J=7.4, 8.4 Hz), 8.20 (dd, 1 H, J 0.6, 0.9 Hz)

EXAMPLE 34

5-([1,3]benzodioxole-5-yl)-1-(3-fluoro-4-methanesulfonylphenyl)-3-trifluoromethyl-1H-1,2,4-triazole

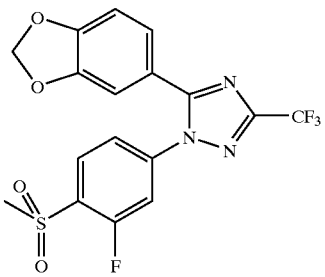

Formula 40

125 mg (yield 77%) of the title compound as a liquid was prepared in the same manner as in Example 22 except using 120 mg of 5-([11,3]benzodioxole-5-yl)-1-(3-fluoro-4-methylsulfanylphenyl)-3-trifluoro methyl-1H-1,2,4-triazole prepared in the example 21 instead of 1-(3-fluoro-4-methylsulfanylphenyl)-5-phenyl-3-trifluoromethyl-1H-1,2,4-triazole.

$^1$H NMR (400 MHz, CDCl$_3$) δ 3.20 (s, 3 H), 6.0 (s, 2 H), 6.80 (s, 1 H), 7.10 (d, 1 H, J=8.1 Hz), 7.40 (d, 1 H$_1$=8.1 Hz), 7.35 (m, 1 H), 8.05 (m, 1 H), 8.15 (m, 1 H)

EXAMPLE 35

1-(3-fluoro-4-methanesulfonylphenyl)-5-(3,4-difluorophenyl)-3-trifluoromethyl-1H-1,2,4-triazole

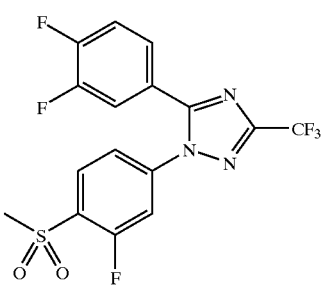

Formula 41

35 mg (yield 27%) of the title compound as a liquid was prepared in the same manner as in Example 22 except using 120 mg of 1-(3-fluoro-4-methylsulfanylphenyl)-5-(3,4-difluorophenyl)-3-trifluoromethyl-1H-1,2,4-triazole instead of 1-(3-fluoro-4-methylsulfanylphenyl)-5-phenyl-3-trifluoromethyl-1H-1,2,4-triazole.

$^1$H NMR (400 MHz, CDCl$_3$) δ 3.20 (s, 3 H) 7.15–7.45 (m, 4 H), 8.05(m, 1 H), 8.15 (m, 1 H)

Experiments

1. Evaluation of selective COX-2 inhibitory activity

1) Method

In order to pharmacologically determine the selective COX-2 inhibitory activity, the percentages of the COX-1 and COX-2 inhibition of the compounds of the present invention illustrated in the Examples were measured by the following methods.

a. Assay for the COX-1 Inhibitory Activity Using U-937

U-937 human lymphoma cells (Korean Cell Line Bank, Seoul, Korea, Accession Number: 21593) were cultured and centrifuged. The collected cells were diluted with HBSS (×1, Hank's balanced salt solution) to a concentration of $1 \times 10^6$ cells/ml. 1 ml of the dilute cell solution was placed into each well of 12-well plates. 5 μl of 1 μM solution of a test compound in DMSO and 5 μl of DMSO as a control were added to the wells. The wells were incubated in $CO_2$ incubator at 37° C. for 15 minutes. Separately, 10 mM stock solution of arachidonic acid in ethanol was diluted ten times in ethanol to prepare 1 mM solution of arachidonic acid. Arachidonic acid acts as a substrate. 10 μl of the 1 mM solution of arachidonic acid was added to each well and incubated at $CO_2$ incubator at 37° C. for 30 minutes. The cell solution of each well was placed in a centrifuge test tube and centrifuged at 10,000 rpm at 4° C. for 5 minutes. The concentration of PGE2 in the collected cells and the supernatant was quantified by means of a monoclonal kit (Cayman Chemicals). The percentages of PGE2 inhibition in a group of the test compound-treated cells in relation to a group of the DMSO-treated cells were calculated. Based on the calculated values, the COX-1 inhibitory activities were evaluated.

b. Assay for the COX-2 Inhibitory Activity Using RAW 264.7 Cell Line $2 \times 10^6$ cells of RAW 264.7 cell line (Korean Cell Line Bank, Seoul, Korea, Accession Number: 40071) were inoculated into each well of 12-well plates. Each well was treated with 250 μM of aspirin and incubated at 37° C. for 2 hours. After the culture media were replaced with new culture media, the new culture media were treated with a test compound (10 nM) and incubated for 30 minutes. Then, each well was treated with interferon γ (100 units/ml) and lipopolysaccharide (LPS, 100 ng/ml) and incubated for 18 hours. The culture media were transferred to other test tubes. The concentration of PGE2 was quantified by means of the EIA kit (Cayman Chemicals).

2) Test Results

The test results are presented in Table 1 below. The percentages of the COX inhibition were calculated according to the following equation:

% Inhibition=(concentration of PGE2 in test compound-untreated sample —concentration of PGE2 in test compound-treated sample)/(concentration of PGE2 in test compound-untreated sample)×100

TABLE 1

| | Cyclooxygenase (COX) Inhibition (%) | |
|---|---|---|
| Samples | COX-1 (1 μM) | COX-2 (10 nM) |
| Reference (Valdecoxib) | 28.8 | 5.47 |
| Example 22 | 32.8 | 13.7 |
| Example 23 | 15.5 | 41.2 |
| Example 24 | 18.8 | 18.5 |
| Example 25 | 19.5 | 13.7 |
| Example 26 | 27.4 | 22.3 |
| Example 27 | 26.4 | 19.0 |
| Example 28 | 25.7 | 15.6 |
| Example 29 | 11.1 | 16.4 |
| Example 30 | 23.2 | 15.1 |

TABLE 1-continued

| | Cyclooxygenase (COX) Inhibition (%) | |
|---|---|---|
| Samples | COX-1 (1 μM) | COX-2 (10 nM) |
| Example 31 | 26.4 | 16.2 |
| Example 32 | 23.2 | 27.8 |
| Example 33 | 44.5 | 13.5 |
| Example 34 | 11.2 | 41.5 |
| Example 35 | 21.2 | 15.5 |

3) Evaluation

The in vitro test results about the percentages of the COX-1 and COX-2 inhibition are listed in Table 1.

As shown in Table 1, inhibition (%) ratios of COX-2 to COX-1 in Examples 22 to 35 were significantly higher than that in the reference, Valdecoxib. This indicates that selective inhibition of COX-2 to COX-1 of the present compound is superior to that of the reference.

The compounds of Examples 22 to 35 exhibited the COX-2 inhibitory activities significantly higher than the reference. Based on this result, it can be seen that the present compounds have reduced side effects due to enhanced selectivity and improved relief effects of fever, pain, and inflammation, compared to the reference.

INDUSTRIAL APPLICABILITY

As apparent from the above description, the present invention provides a 1,2,4-triazole derivative or a non-toxic salt thereof, a preparation method thereof, and a pharmaceutical composition containing the derivative or the salt as an active ingredient. The pharmaceutical composition is effective in reducing fever, pain, and inflammation. In particular, as a result of reduction of the side effects of conventional nonsteroidal antiinflammatory agents, the pharmaceutical composition is useful for treating patients with peptic ulcer disease, gastritis, regional enteritis, ulcerative colitis, diverticullitis, gastrorrhagia, or hypoprothrombinemia.

While the present invention has been particularly shown and described with reference to exemplary embodiments thereof, it will be understood by those of ordinary skill in the art that various changes in form and details may be made therein without departing from the spirit and scope of the present invention as defined by the following claims. 39%)

What is claimed is:

1. A 1,2,4-triazole derivative represented by formula 1:

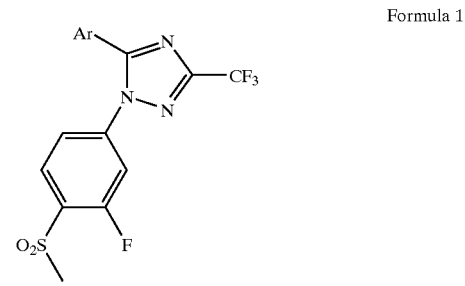

Formula 1 wherein, Ar represents naphthyl; 3,4-methylenedioxyphenyl; phenyl; or plenyl substituted with the group selected from $C_1$–$C_6$ alkyl, $C_1$–$C_6$ alkoxy, or halogen;

or a non-toxic salt thereof.

2. The 1,2,4-triazolo derivative according to claim 1, which is selected from the group consisting of:

- 1-(3-fluoro-4-methanesulfonylphenyl)-5-phenyl-3-trifluoromethyl-1H-1,2,4-triazole;
- 1-(3-fluoro-4-methanesulfonylphenyl)-5-(4-methoxyphenyl)-3-trifluoromethyl-1H-1,2,4-triazole;
- 1-(3-fluoro-methanesulfonylphenyl)-5-(4-fluorophenyl)-3-trifluoromethyl-1H-1,2,4-triazole;
- 1-(3-fluoro-4-methanesulfonylphenyl)-5-(4-bromophenyl)-3-trifluoromethyl-1H-1,2,4-triazole;
- 1-(3-fluoro-4-methanesulfonylphenyl)-5-(4-chlorophenyl)-3-trifluoromethyl-1H-1,2,4-triazole;
- 1-(3-fluoro-4-methanesulfonylphenyl)-5-(4-methylphenyl)-3-trifluoromethyl-1H-1,2,4-triazole;
- 1-(3-fluoro-4-methanesulfonylphenyl)-5-(4-ethoxyphenyl)-3-trifluoromethyl-1H-1,2,4-triazole;
- 1-(3-fluoro-4-methanesulfonylphenyl)-5-(3-chlorophenyl)-3-trifluoromethyl-1H-1,2,4-triazole;
- 1-(3-fluoro-4-methanesulfonylphenyl)-5-(3-fluorophenyl)-3-trifluoromethyl-1H-1,2,4-triazole;
- 1-(3-fluoro-4-methanesulfonylphenyl)-5-(3-fluoro-4-methoxyphenyl)-3-trifluoromethyl-1H-1,2,4-triazole;
- 1-(3-fluoro-4-methanesulfonylphenyl)-5-(3-methylphenyl)-3-trifluoromethyl-1H-1,2,4-triazole;
- 1-(3-fluoro-4-methanesulfonylphenyl)-5-(naphthalene-2-yl)-3-trifluoromethyl-1H-1,2,4-triazole;
- 5-([1,3]benzodioxole-5-yl)-1-(3-fluoro-4-methanesulfonylphenyl)-3-trifluoromethyl-1H-1,2,4-triazole; and
- 1-(3-fluoro-4-methanesulfonylphenyl)-5-(3,4-difluorophenyl)-3-trifluoromethyl-1H-1,2,4-triazole;

or a non-toxic salt thereof.

3. A pharmaceutical composition comprising:

administering a therapeutically effective amount of a 1,2,4-triazole derivative or a ion-toxic salt thereof according to claim 1; and a pharmaceutically acceptable carrier.

4. A pharmaceutical composition comprising:

administering a therapeutically effective amount of 1,2,4-triazole derivative or a non-toxic salt thereof according to claim 2; and a pharmaceutically acceptable carrier.

* * * * *